(12) United States Patent
Berg et al.

(10) Patent No.: US 7,898,670 B2
(45) Date of Patent: Mar. 1, 2011

(54) DISTORTION MEASUREMENT IMAGING SYSTEM

(75) Inventors: David Berg, Rochester, NY (US); Jacques Gollier, Painted Post, NY (US); Douglas S Goodman, Pittsford, NY (US); Correy Robert Ustanik, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 240 days.

(21) Appl. No.: 12/072,385

(22) Filed: Feb. 26, 2008

(65) Prior Publication Data

US 2008/0204740 A1    Aug. 28, 2008

Related U.S. Application Data

(60) Provisional application No. 60/903,443, filed on Feb. 26, 2007.

(51) Int. Cl.
*G01B 9/02* (2006.01)

(52) U.S. Cl. ...................... 356/492; 356/616

(58) Field of Classification Search ............... 356/492, 356/493, 495, 496, 498, 506, 508, 511, 513, 356/514, 139, 616
See application file for complete search history.

(56) References Cited

U.S. PATENT DOCUMENTS

| | | | |
|---|---|---|---|
| 4,566,762 A | 1/1986 | Kato | 350/411 |
| 5,073,021 A | 12/1991 | Marron | 351/168 |
| 5,757,459 A | 5/1998 | Bhalakia et al. | 351/168 |
| 6,236,633 B1 | 5/2001 | Chang et al. | 369/112 |
| 6,426,838 B1 | 7/2002 | Rudeen | 359/487 |
| 6,654,061 B2 | 11/2003 | Yamada | 348/355 |
| 6,674,522 B2 | 1/2004 | Krantz et al. | 356/237 |
| 6,685,315 B1 | 2/2004 | De Carle | 351/161 |
| 6,882,432 B2 * | 4/2005 | Deck | 356/512 |
| 7,035,009 B1 | 4/2006 | Kelly et al. | 359/484 |
| 2002/0024673 A1 * | 2/2002 | Ouchi | 356/495 |
| 2003/0031110 A1 | 2/2003 | Ishizuka | 369/112.26 |
| 2003/0053066 A1 | 3/2003 | Redner | 356/448 |
| 2004/0021863 A1 | 2/2004 | Kurata et al. | 356/364 |
| 2005/0177339 A1 * | 8/2005 | Kuhn | 702/167 |
| 2005/0219522 A1 | 10/2005 | Jones | 356/239.1 |
| 2006/0126077 A1 * | 6/2006 | Ueki et al. | 356/512 |
| 2006/0203251 A1 * | 9/2006 | Millerd et al. | 356/495 |
| 2006/0247891 A1 | 11/2006 | Fox et al. | 702/155 |

* cited by examiner

*Primary Examiner*—Tarifur Chowdhury
*Assistant Examiner*—Jonathan M Hansen
(74) *Attorney, Agent, or Firm*—Thomas R. Beall (57) ABSTRACT

A distortion measurement and inspection system is presented. In one embodiment, a vision system is implemented. The vision system performs dual focal plane imaging where simultaneous imaging of two focal planes is simultaneously performed on a sample substrate and a reference substrate to determine distortion. In addition, a highly reflective background is implemented to provide for more resolution during distortion measurement.

18 Claims, 8 Drawing Sheets

DISTORTION MEASUREMENT IMAGING SYSTEM

RELATED APPLICATION

This application claims the benefit of and priority to U.S. Patent Application Ser. No. 60/903,443 filed on Feb. 26, 2007, the contents of which are relied upon and incorporated herein by reference in its entirety.

BACKGROUND OF THE INVENTION

1. Field of the Invention

The present invention is directed to a distortion measurement imaging system.

2. Technical Background

Liquid Crystal Displays (LCDs) are a popular modern technology. LCDs are used in many display devices including televisions and computers. LCD glass manufacturing is a very intricate process. Extremely restrictive controls are needed to meet the tolerance requirements that are necessary to produce glass that is useable in television or computer applications, such as liquid crystal displays (LCDs). As such, measurement and inspection is a key process step in the manufacture of LCDs and the technologies used to enable the measurement and inspection process are key components of any LCD manufacturing operation. One key measurement and inspection device is used to measure distortion in LCD glass. Distortion may occur during manufacturing for many reasons. Among the reasons are heat or thermal manufacturing cycles. Cutting the glass can create stresses and distort the glass.

One measurement and inspection device uses relative measurement to measure the distortion in an LCD substrate. The conventional measurement and inspection device includes a support table used to support the substrate and vacuum the substrate down so that the substrate does not move. The support table includes reference markings and means that can be used to place an inscription on the substrate. A process is then performed on the substrate and the substrate is repositioned on the support table. A comparison can then be made between the inscription on the substrate and the reference marking to determine the amount of distortion.

Figure 1:
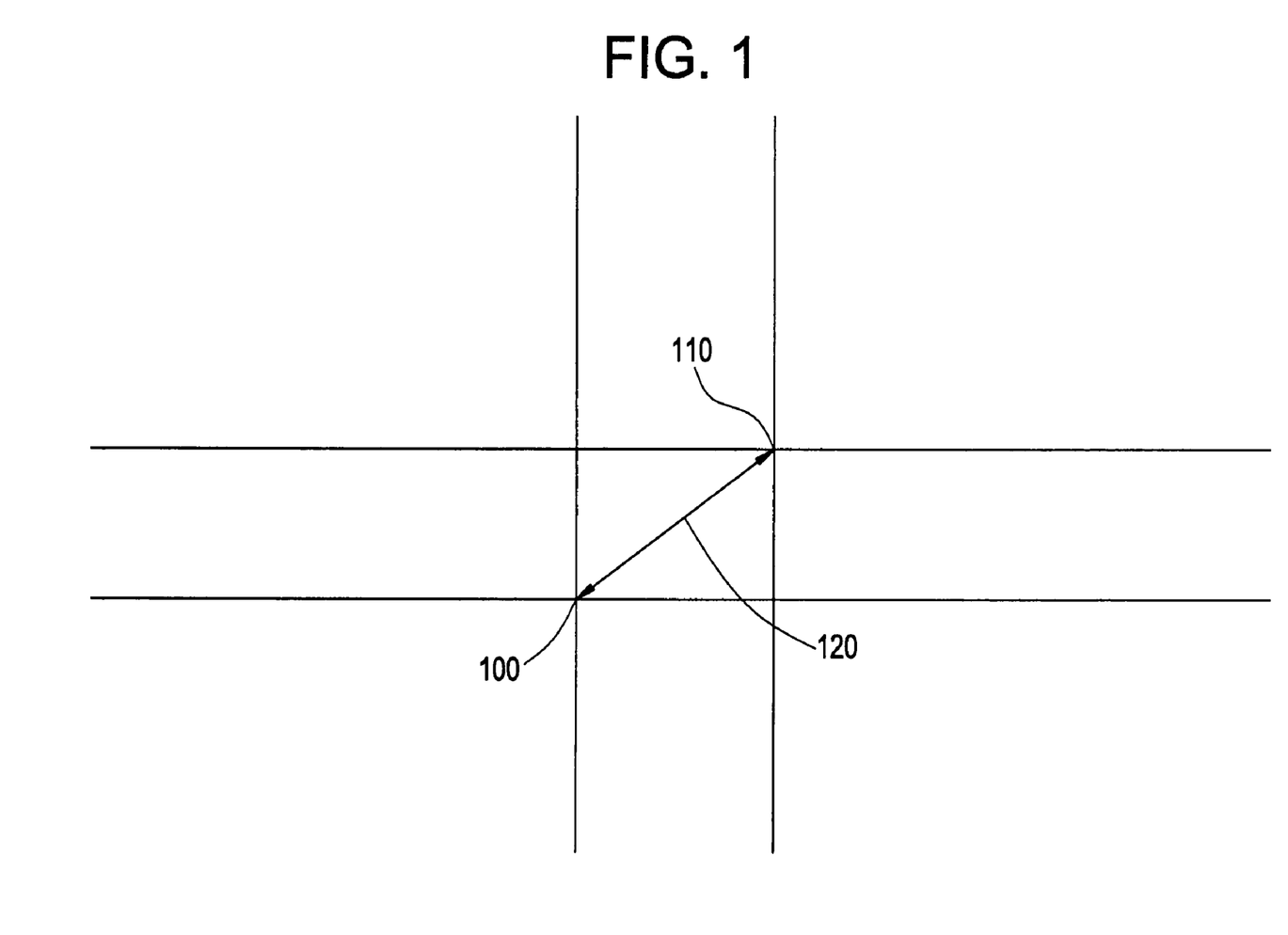
FIG. 1 displays a prior art drawing of a measurement node.

Generally speaking relative measurement includes using a reference plate that has a target grid pattern such as the support plate mentioned above. A sample LCD glass substrate is then placed on the top of the reference plate. The sample substrate has the similar target grid pattern. The reference plate grid and the sample glass grid are offset with respect to each other. The vector distance between the reference plate grid target and the sample glass grid target is referred to as a measurement node. FIG. 1 displays a prior art example of the reference glass grid, the sample glass grid, and the vector distance between the two. As shown in FIG. 1 a reference glass grid 100 is shown. A sample glass grid is also shown as 110. The vector distance 120 (i.e., measurement node) between the reference glass grid 100 and the sample glass grid 110 is also shown.

Conventional distortion measurement is performed in two stages. The first stage includes measuring each node on the glass substrate relative to the grid pattern on the support table. Given the sub micron accuracies required, optical devices such as cameras are employed to distinguish the grid patterns and observe changes in the measurement node. The first stage occurs prior to performing a process on the glass sample such as plate cutting or thermal cycling. Once this process has occurred, the second stage occurs. The second stage includes measuring each node on the glass substrate relative to the grid pattern on the support table. The distortion of the glass can then be calculated by measuring any changes in the measurement node between the first stage and the second stage. In order to determine the glass deformation, the difference in measurements between the first and second stages needs to be corrected of pure translation and rotations.

Figure 2:
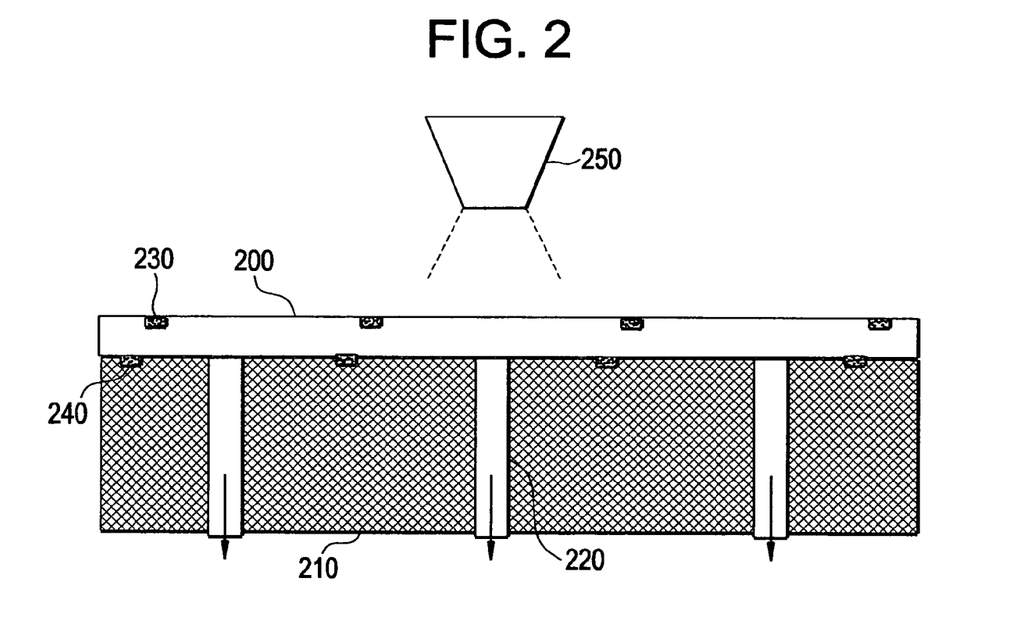
FIG. 2 displays a prior art drawing of a measurement and inspection system.

FIG. 2 displays a magnified view of the components used in distortion measurement. A sample substrate 200 is shown. At step one, the sample substrate 200 is positioned on a reference substrate 210. At step two, the grid 230 is scribed on the sample substrate 200. The reference substrate 210 includes vacuum ports shown as 220. A first grid pattern 230 is shown on the sample substrate 200. A second grid pattern 240 is shown on the reference substrate 210. A vision system 250 such as a camera is shown. At step three, the sample substrate 200 is flipped over so that the grid patterns (230, 240) face each other and the position of the first grid pattern 230 is measured relative to the second grid pattern 240 using the vision system 250. At step four, the sample substrate 200 is then removed, a process is performed (i.e., cutting, thermal cycle). At step five, the sample substrate 200 is repositioned with the grid patterns facing each other as in step three and re-measured. The difference in measurement (i.e., the measurement node) between step three and step five is the distortion of the sample substrate.

A target grid on the sample substrate being tested is marked on its top surface. The sample substrate thicknesses range from 0.4 mm to 1.1 mm. Both target grids are simultaneously measured to reduce measurement error. Therefore, conventional methods flip the sample substrate so that the grid of the sample substrate is in the same focal plane as the grid of the reference substrate. Aligning the target grids (i.e., producing an offset between the grids of approximately +/−50 um throughout the entire sheet) for large sized substrates after flipping is extremely challenging and as a result special handling technology is required.

In addition to the issues associated with flipping or reversing the substrate additional issues are encountered in distinguishing the reference grid pattern and the sample grid pattern using conventional vision systems. Specifically, flipping the sample substrate and placing the grid pattern of the sample substrate on the same focal plane as the reference substrate reduces the ability of the vision system to distinguish and contrast the two grid patterns. Conventional lighting for imaging the target grids utilizes brightfield Kohler illumination. This causes a bright background (i.e., reflections off of the substrate) and a dark foreground (i.e., target grid scattering outside the NA of the imaging lens). This background is susceptible to two main factors that lower the contrast of the target grid. First, during measurement, a vacuum is applied to the bottom surface of the sample glass substrate. This is required to ensure that there is no relative displacement between the sample and reference plate as well as to impose a consistent shape on the sample substrate. The resulting gap between the two substrates is minimized to submicron levels which will allow interference to occur between the two surfaces which can seriously degrade the contrast of the imaged measurement nodes. Second, the top surface of the reference substrate is prone to contamination such as scratches from multiple sources such as, flipping the sample substrate, cleaning, dust, etc. This also degrades the image and contrast between the grid pattern of the sample substrate and the reference substrate. Even more important than contrast and image quality degradation, those interferences and dust will be different from the first and second measurements. They will then affect the node measurement a different way for the two measurements resulting in significant measurement errors.

Thus it would be beneficial to address the problems associated with flipping a substrate. For example, it would be beneficial to address the mechanical, handling, alignment, and imaging problems associated with flipping and measuring a substrate for distortion.

SUMMARY

A method and apparatus are presented for addressing the mechanical, handling, alignment, and imaging problems associated with flipping a substrate for measurement and inspection. In accordance with the teachings of the present invention an imaging method and a contrast enhancing assembly are used to eliminate the need for flipping the substrate. In one embodiment a dual focal plane imaging method is used to determine distortion. In a second embodiment a highly reflective homogeneous surface is applied to the back side of the reference substrate to create a contrast enhancing assembly. It should be appreciated that each embodiment may be used separately or in combination to address the problems associated with flipping the substrate.

In accordance with the teachings of the present invention, dual focal plane imaging is implemented into a glass measurement and inspection system. In one embodiment, dual focal plane imaging is implemented to provide high resolution by simultaneously imaging target grids on both the sample substrate and the reference substrate which in turn provides two distinct focal planes separated by the width of the substrate (i.e., from 0.4 mm to 1.1 mm along an optical axis). A variety of methods may be implemented to perform dual focal plane imaging such as polarization multiplexing, color multiplexing, etc.

In accordance with the teachings of the present invention a contrast enhancing assembly is presented which includes a highly reflective homogeneous surface positioned on an oppositely disposed side of a reference substrate from the imaging system. The high reflectivity (i.e., mirror surface) is used to minimize contrast variation between the sample substrate and the reference substrate due to interference and contamination. It should be appreciated that in an alternate embodiment a highly reflective diffuse surface such as a bright white surface may also be implemented.

In one embodiment an imaging system is disclosed. The imaging system includes an imaging optics subsystem and an illumination optics subsystem. The imaging system is used for focal plane combination, magnification, illumination, light generation, image formation and image detection.

As a result of the sub-micron levels of distortion and accuracy required, in accordance with the teachings of the present invention a magnification of approximately 15× and a numerical aperture (NA) of approx 0.1 is required to distinguish the distortion (i.e., changes in measurement nodes) in the substrate. Achieving the required magnification and NA requires a depth of focus of approximately 88 um.

BRIEF DESCRIPTION OF THE DRAWINGS

The accompanying drawings, which are incorporated in and constitute a part of this specification, illustrate certain aspects of the instant invention and together with the description, serve to explain, without limitation, the principles of the invention.

DETAILED DESCRIPTION

In accordance with the teachings of the present invention a dual focal plane vision system is implemented in a glass measurement and inspection system. In one embodiment, a measurement and inspection system such as one disclosed in a method and apparatus for measuring dimensional changes in transparent substrates, filed Apr. 28, 2005, Publication number 20060247891A1, assigned to Corning Incorporated is incorporated by reference.

The dual focal plane imaging system includes both a dual focal plane generation system and a dual focal plane detection system. A dual focal plane vision system may be thought of as any vision system that facilitates simultaneous imaging of two object focal planes into one detector image plane that can clearly measure the two grid patterns at a submicron level. In one embodiment, nodes are measured without regard to which grid pattern is the reference and which is the substrate. In accordance with the teachings of the present invention a dual focal plane system may be implemented using polarization multiplexing, color multiplexing, or with a faux interferometer configuration.

In accordance with the teachings of the present invention, a sample substrate and a reference substrate are positioned contiguous to each other, forming an interface with each other at the plane of contact. The sample substrate is positioned closer to an imaging plane than the reference substrate. The front side of the sample substrate forms a first focal plane and the front side of the reference substrate (i.e., the side in contact with the sample substrate) forms a second focal plane. In one embodiment, the first focal plane and the second focal plane are referred to as dual focal planes. The sample substrate and the reference substrate include markings that convey position information, such as scribed lines. The relative position of these markings, measured at various points in time, convey information about the relative shape of the sample substrate with respect to the reference substrate. In addition, position information may also include width and length of the respective substrates, the lateral and horizontal position of the substrates relative to each other, etc. Position information may include any information that describes the physical boundaries of the substrate and/or the orientation of the substrate.

Incident light is directed at the dual focal planes. The incident light is reflected from the dual focal planes and produces reflected light. In one embodiment, the reflected light comprises at least two coincident beams of orthogonally polarized light. In accordance with the teachings of the present invention, coincident is a geometric term that defines the relationship between the two light beams: the two light beams lie one on top of the other occupying substantially the same space and time. The two beams are distinguished one from the other by a non-geometrical attribute, i.e. direction of polarization.

At least two of the coincident beams of orthogonally polarized light traverse through a substantially common optical path. In one embodiment, of the present invention traversing through a substantially common optical path describes two light beams occupying the same space and traversing at the same time through the same element or components; where the same space is defined as a space where the movement of the components would cause image motion less than the distortion to be measured and the same time is defined as a time between the two measurements that is less than the time that the image can move more than the distortion being measured. In accordance with the teachings of the present invention space measurements are defined and detected on a nanometer scale.

After traversing through the substantially common optical path the position information from the dual focal planes is precisely reproduced on a single image plane, where a precise reproduction is a reproduction that is at a level that is less than the distortion we are trying to measure. In one embodiment, the image plane is implemented with at least one detector. As a result, a 1-to-1 relationship is developed between position information associated with the focal planes (i.e., reference markings, relative position information, etc) and positions on the image plane. In one embodiment, constructing this 1-to-1 relationship may be defined as imaging. It should be appreciated that at least a 1-to-1 relationship is discussed and described in the application; however, this does not preclude a situation where a one-to-many relationship is defined.

In another embodiment, an optical path is defined. Optical components are positioned along the optical path. A dual focal plane assembly is positioned on one end of an optical path and an image plane is positioned on an oppositely disposed end of the optical path from the dual focal plane (i.e., the other end of the optical path). In accordance with the teachings of the present invention, light is reflected off of the dual focal planes that are positioned relative to each other (i.e., producing position information) and traverses through the optical path to the image plane. As such, imaging is defined as reflecting the light off the dual focal planes, processing the reflected light through a substantially common optical path and then constructing a 1-to-1 relationship at an image plane positioned on the opposite end of the optical path from the dual focal planes.

Creating the 1-to-1 mapping relationship at the nanometer level enables a number of different types of measurement of the dual focal plane. For example, the substrate may be imaged and then a process such as thermal cycling may be performed on the substrate. When the substrate is repositioned the sample substrate may be imaged once again and distortion measurements may be acquired.

Figure 3:
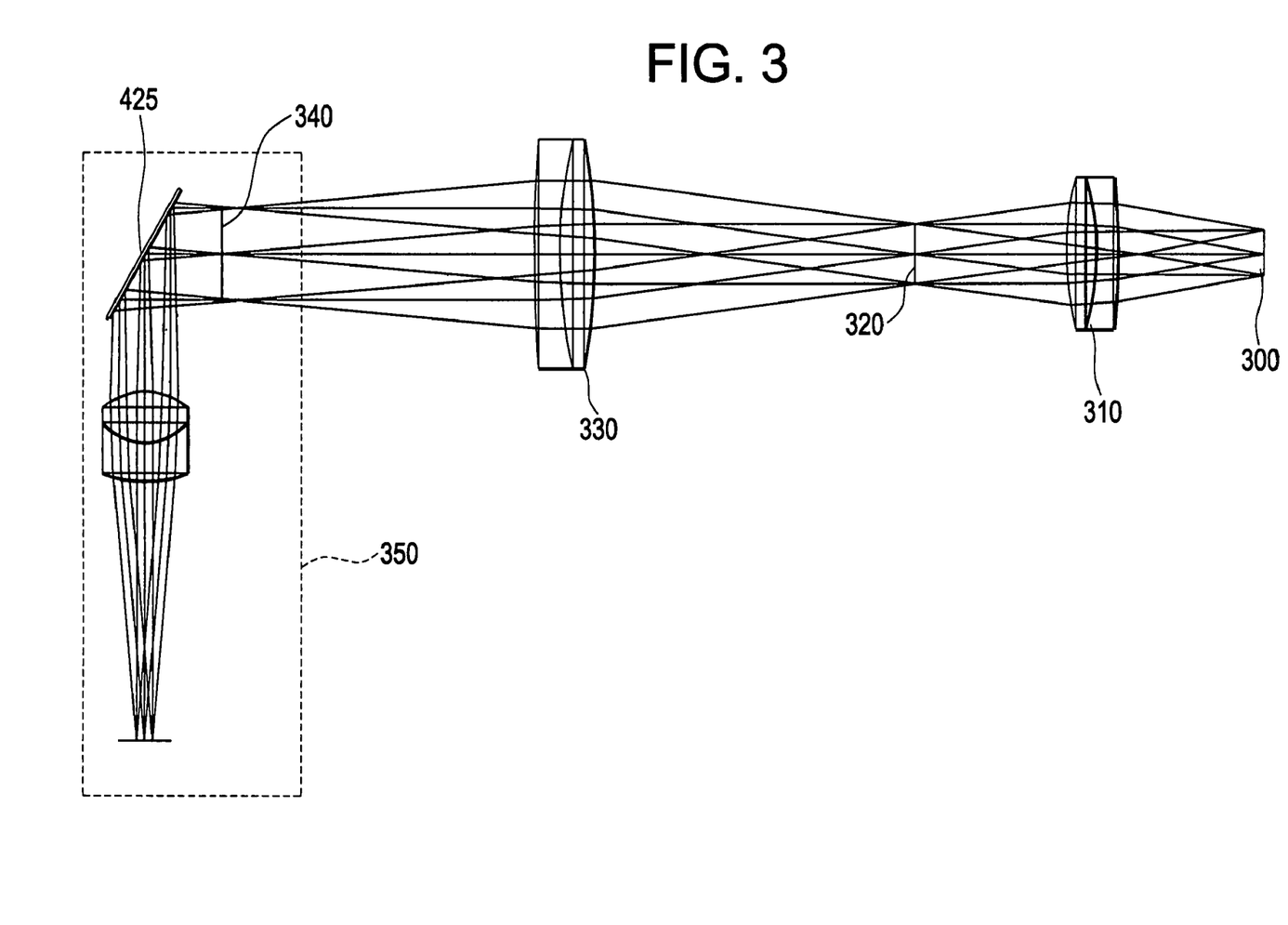
FIG. 3 displays an illumination subsystem implemented in accordance with the teachings of the present invention.
Figure 4:
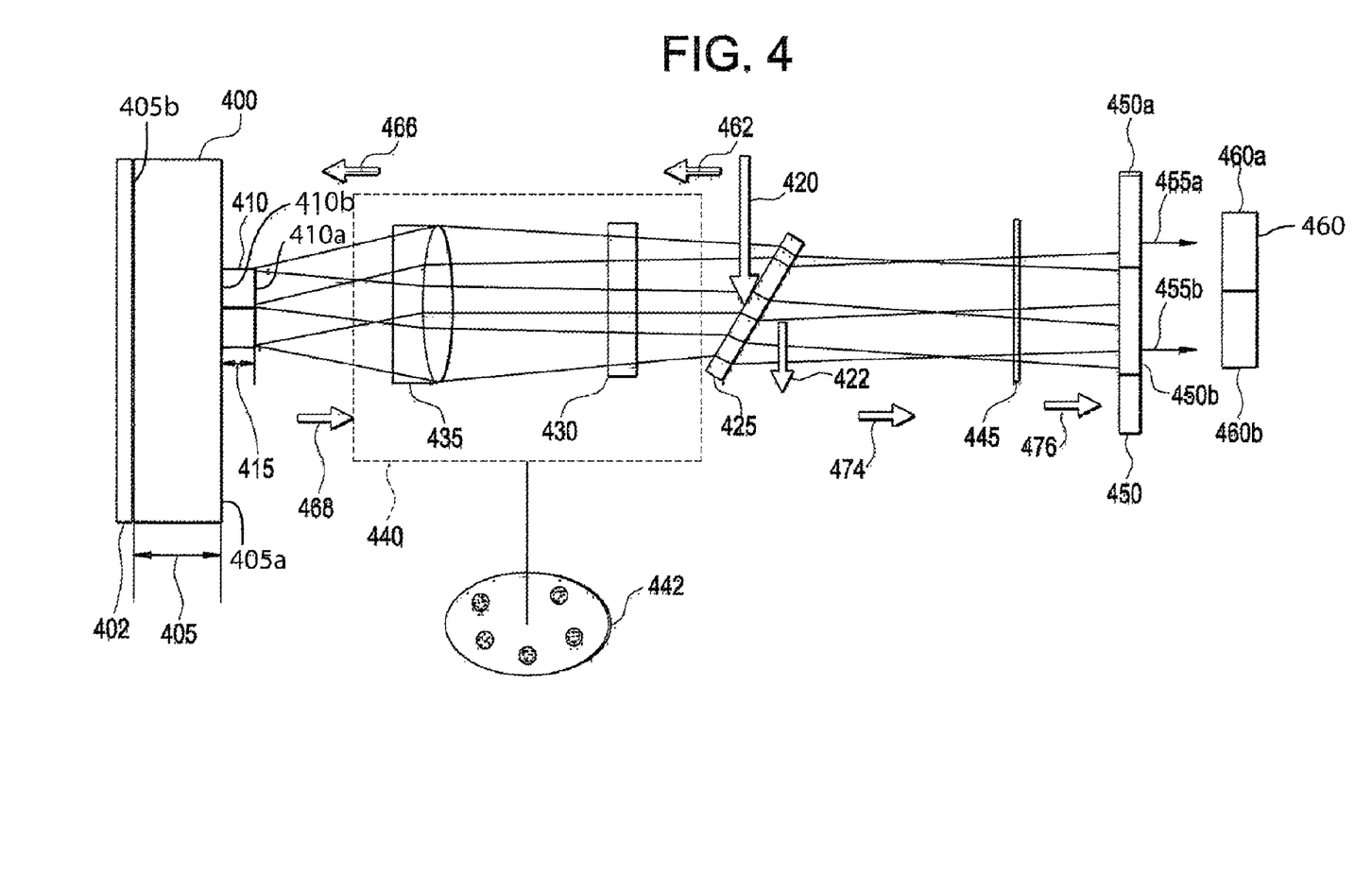
FIG. 4 displays an imaging subsystem implemented in accordance with the teachings of the present invention.

In one embodiment, an illumination optics subsystem includes an illumination optics path shown in FIG. 3 and an imaging optics subsystem including an imaging optics path shown in FIG. 4. In one embodiment, the illumination optics subsystem of FIG. 3 produces bright field reflective Kohler illumination. Both the illumination optics path and imaging optical paths have individual aperture stops to provide the capability of adjusting the sigma values of the system. The sigma value is the ratio of the illumination numerical aperture (NA of the illumination optics path) to the image numerical aperture (NA of the imaging optics path). A higher sigma value results in overfilled imaging pupil making the illumination uniform throughout lateral and focus variation changes.

FIG. 3 displays an illumination optics subsystem implemented in accordance with the teachings of the present invention. The illumination optics subsystem detailed in FIG. 3 produces a homogeneous on-axis telecentric illumination. In one embodiment, the illumination optics subsystem produces broadband, medium intensity, stable, on-axis, telecentric light, where the numerical aperture can be controlled. Numerical aperture is a description of the range of angles over which a system can accept or emit light. A telecentric lens may be defined as a lens in which the rays through the center of the entrance or exit pupil of the lens are all parallel to the optical axis, on one or both sides of the lens, no matter at which part of the image or object planes they terminate or originate. In other words, telecentric imaging and telecentric illumination produce light that has all central rays parallel to the optical axis. The optics subsystem is disposed so that its optic axis is orthogonal to the focal plane. In one embodiment, the elements such as lenses and apertures, used to manipulate the generated light in the illumination optics subsystem form a path referred to as the illumination path.

A white light emitting diode (LED) illumination source 300 is shown. In one embodiment, a white LED 300 that produces a broad band of light that is consistent in amplitude and generates approximately 3 watts of power is implemented. Although a white LED 300 is disclosed it should be appreciated that any polychromatic light source that avoids coherence to minimize Netown's rings may be implemented in accordance with the teachings of the present invention.

A doublet lens 310 is shown. The condensing lens 310 is used to collimate the light generated by the white LED 300. A field stop is integrated at location 320 where the beams emitted by all points of the source converge. This field stop is imaged through lenses 330 and 350 on the object to illuminate. So, by adjusting the size of the field stop, the size of the object that gets illuminated can be adjusted.

A second lens 330 reimages the source on an intermediate position 340 where a second aperture called the aperture stop is located. The diameter of the aperture stop controls the NA of the illumination. The aperture stop is located in the rear focal plane of lens 360, so that rays from the center of the aperture stop emerge parallel to the optical axis of this lens on the object side. Thus the location of the aperture stop causes the illumination path to be telecentric on the object side.

This illumination system known as a Kohler illumination allows control of the size and the NA of the illumination, insures uniform illumination, and also insures a telecentric illumination, meaning that each point of the object is illuminated by a cone of light whose direction is perpendicular to the object.

The mirror (425) can eventually be a 50% beam splitter allowing to collect the light reflected by the object through the beam splitter. The imaging system displayed on FIG. 4 can then be used in conjunction with the illumination system displayed on FIG. 3 to provide, in the same instrument, the illumination and the imaging functions.

FIG. 4 displays an imaging optics subsystem of a dual focal point imaging system implemented in accordance with the teachings of the present invention. The imaging optics subsystem provides a means of combining two focal planes into at least one detector. In one embodiment, polarization multiplexing is used to implement a dual focal plane vision system. In one embodiment a birefringence lens is used to implement the polarization multiplexing. The birefringence lens implemented in accordance with the teachings of the present invention is used to split an initial beam using imaging optics onto two different focal planes. The birefringence lens has a different index of refraction depending on the orientation of the polarization-vector of the incident ray of light. As a result the birefringence lens decomposes an incident ray of light into two rays (i.e., often called the ordinary ray and the extraordinary rays). Using birefringence lenses to image two objects located at different axial positions is known and is, for instance, described in U.S. Pat. No. 4,566,762A and U.S. Pat. No. 5,073,021A.

If a single birefringence lens element is used, then light rays of both polarizations will experience a wavelength dependent shift known as lateral chromatic aberration. In order to control this aberration, the optical power of the birefringence lens is minimized. In one embodiment, this is accomplished by first collimating the light beam emitted by the object and then using a low optical power birefringence lens located where the beam is collimated.

In FIG. 4 a reference substrate 400 is shown and a sample substrate 410 is shown. In accordance with the teachings of the present invention, the reference substrate 400 is implemented with alumino-borosilicate display glass. The reference substrate 400 may have a thickness 405 which is about 6.8 mm, and the sample substrate 410 may have a thickness 415 of about 0.7 mm. The sample substrate 410 is implemented with alumino-borosilicate family of glasses such as Corning 1737, Corning Eagle 2000, etc, which are trademarks of Corning Incorporated. The sample substrate has a front-side or first focal plane shown as 410a and a backside or second focal plane shown as 410b. For the purposes of discussion, light is reflected off of the front focal plane 410 and off of the back focal plane 410b. In one embodiment, the second focal plane 410b is implemented by the contiguous placement of the substrate 410 and the reference substrate 400. It should also be noted that the reference substrate 400 also includes a front side 405a and a back side 405b. In one embodiment of the present invention the interface between the backside 410b of the sample substrate 410 and the front side 405a of the reference substrate 400 form the second focal plane.

Illuminating light 420 is shown as entering the imaging subsystem shown as FIG. 4. In one embodiment, the illuminating light 420 is generated by the illuminating optics subsystem of FIG. 3. A non-polarizing plate beam splitter 425 receives the illuminating light 420 and directs the illuminating light 420 onto the various object planes. The illuminating light 420 passes through the birefringence lens 430 and the doublet objective 435. The light is then reflected from the respective focal planes 410a and 405a, and back through the doubled objective. The birefringence lens 430 serves as a corrective converging lens so that that the light can combine appropriately at the imager. An aperture 445, a demultiplexer 450, and a CCD detector 460 are also shown. The beam splitter 425, the birefringence lens 430, the image doublet 435, the aperture 445, the demultiplexer 450 and the CCD detector 460 are each positioned along the imaging path.

During operation, the illuminating optics subsystem shown in FIG. 3 generates the illuminating light 420 shown in FIG. 4. The illuminating light 420 illuminates the beam splitter 425. As shown by 462 50% of the illuminating light 420 is directed along a forward path to the birefringence lens 430 and 50% shown by 422 is directed toward a beam dump. Light passes through the birefringence lens 430 and the doublet 435 focuses the light onto the sample 410.

In one embodiment, in the reverse direction the reflected light 468 is processed through the image doublet 435 which is so disposed that the system magnifies the object (i.e., 15×-19×) in the CCD plane 460. The light passes through the birefringence lens 430, which has two different indices of refraction that act on the two different orthogonal polarizations of light, first and second. The larger of these two indices acts on said first orthogonal polarization so that light of said first polarization reflecting from said top of sample 410 is correctly focused in said CCD plane 460. The smaller of these two indices acts on said second orthogonal polarization so that light of said second polarization reflecting from said interface between sample 410 and said reference substrate 400 is correctly focused in said CCD plane 460. In one embodiment, a turret 442 is used to rotate a stage 440 including the doublet 435 and the birefringence lens 430 so that different doublets 435 and birefringence lenses 430 that are adjusted for correct focusing with sample substrate thicknesses 415 can be substituted into the imaging path.

In the reverse direction, at the beam splitter 425, 50% of the signal 468 is reflected back to the illumination optics subsystem and 50% traverses the reverse path (i.e., shown as 474) in the direction of the aperture stop 445. The aperture stop 445 facilitates the control of the numerical aperture of the image optics. The aperture stop 445 also provides the flexibility to adjust the image quality by changing (i.e., fine tuning) the contrast or manipulating the sigma value.

A demultiplexer 450 receives the light 476 from the aperture stop 445 that corresponds to the two different focal planes. The light 476 includes two light paths with different polarizations that share the same optical axis. Each focal plane (i.e., 410a, 410b) is associated with light of a different polarization. The demultiplexer includes a first portion 450a and a second portion 450b. The first portion 450a passes light with the first orthogonal polarization and the second portion of the demultiplexer 450b passes the second portion 450b.

The demultiplexer 450 accomplishes a number of objectives, for example, the demultiplexer separates the light corresponding to the two different focal planes; the demultiplexer keeps the contrast level high; and using the demultiplexer helps to avoid including information from one focal plane onto another focal plane. The demultiplexer receives the light at different polarizations and separates the light of the different polarizations. A first portion of the demultiplexer 450a receives and processes the light from one polarization. A second portion of the demultiplexer 450b receives and processes the light from a second polarization. The demultiplexer then generates a first polarized light 455a and a second polarized light 455b.

Lastly, in the reverse path, the first polarized light 455a and the second polarized light 455b are communicated to an image plane 460 which in one embodiment may be implemented with a detector. In accordance with the teachings of the present invention, the first polarized light 455a and the second polarized light 455b are combined at the image plane 460, for example with a detector. A first portion of the image plane 460a receives and processes the first polarized light 455a and the second portion of the image plane 455b receives and processes the second polarized light 460b.

In a second embodiment, a first, second, third and fourth polarized light beam is reflected (i.e., as shown by 468). The first and second beams of polarized light are reflected from the first focal plane 410a and the third and fourth beams of polarized light are reflected from the second focal plane 410b.

In one embodiment the light 466 includes two light beams of orthogonal polarization. The two light beams of orthogonal polarization reflect off of the first focal plane 410a and off of the second focal plane 410b. Reflected light 468 is shown to generally depict light reflecting off of the various focal planes (i.e., 410a, 410b) and the highly reflective surface 402.

Two coincident light beams of orthogonal polarization reflect off of the first focal plane 410*a* and traverse through doublet objective 435. The two coincident light beams of orthogonal polarization, which are generally depicted by reflected light 468 are processed through doublet objective 435, which provides optical power/magnification. At the birefringence lens 430, the two coincident light beams of orthogonal polarization will see two different indices of refraction. In one embodiment, the light 466 reflected off of the first focal plane 410 (two coincident light beams of orthogonal polarization) are processed by the high index of refraction or high optical power portion of the birefringence lens 430. As a result the two coincident beams of orthogonal polarization will be focused at slightly different distances. The coincident beam of orthogonal polarization processed through the higher index of refraction will be focused at the detector 460 (i.e., focal plane). The other coincident beam of orthogonal polarization will be focused beyond the detector 460. It should be noted that in one embodiment of the present invention, the demultiplexer 450 will pass the first beam and block the second beam. Although the relative focal positions of the two coincident beams of orthogonal polarization have been changed the two coincident beams of orthogonal polarization are still traveling on the same optical axis.

Another two coincident light beams of orthogonal polarization (i.e., a third and a fourth beam) reflect off of the second focal plane 410*b* and traverse through doublet objective 435. The two coincident light beams of orthogonal polarization, which are generally depicted by reflected light 468 are processed through doublet objective 435, which provides optical power/magnification. At the birefringence lens 430, the two coincident light beams of orthogonal polarization will see two different indices of refraction. In one embodiment, the light 466 reflectived off of the second focal plane 410 (two coincident light beams of orthogonal polarization) are processed by the low index of refraction or low optical power portion of the birefringence lens 430. As a result the two coincident beams of orthogonal polarization will be focused at slightly different distances. The coincident beam of orthogonal polarization processed through the lower index of refraction (i.e., third beam) will be focused at the detector 460 (i.e., focal plane). The other coincident beam of orthogonal polarization (i.e., fourth beam) will be defocused before the detector 460. It should be noted that in one embodiment of the present invention, the demultiplexer 450 will pass the third beam and block the fourth beam. Although the relative focal positions of the two coincident beams of orthogonal polarization have been changed the two coincident beams of orthogonal polarization are still traveling on the same optical axis.

In a third embodiment, the light 466 illuminates the sample 410 after traversing the forward path and reflects from three planes. The top surface of the sample 410 reflects light, the interface between the sample 410 and the reference substrate 400 reflects light; and the highly reflective surface 402 reflects light. All three reflections produce a reflected light 468, which is proportional to the incident light 466 entering the sample in the forward path.

It should be appreciated that a common optical path is shown between reflected light 468 and light 476. A substantially common optical path is then shown between 450 and 460, where the different beams or orthogonal polarization are separated and impact the image plane 460 at different locations.

In accordance with the teachings of the present invention, a variety of detection methods may be implemented at the focal plane 460. In one embodiment, a polarizing beam splitter is positioned after the aperture stop 445 and the two polarization light paths are sent to two different CCD cameras positioned at the same focal distance. In a second embodiment, a polarizer is placed in front of the sensitive area of the CCD camera so that one portion of the sensitive area receives light with one direction of polarization (i.e., first orthogonal polarization) and the other portion of the sensitive areas receives light with another direction of polarization (i.e., second orthogonal polarization). In a third embodiment, a switching method (i.e., liquid crystal device or a polarizer put on a rotating wheel) may be implemented so that the sensitive area is illuminated by the light of the first orthogonal polarization for a certain period of time and the sensitive area is illuminated by the light of the second orthogonal polarization for a different time period. In one embodiment, measurements of plates with different plate thicknesses is achieved by using the birefringence lens focal length to achieve a separation of the ordinary and extraordinary focal planes which correspond to the sample substrate thickness.

Figure 5:
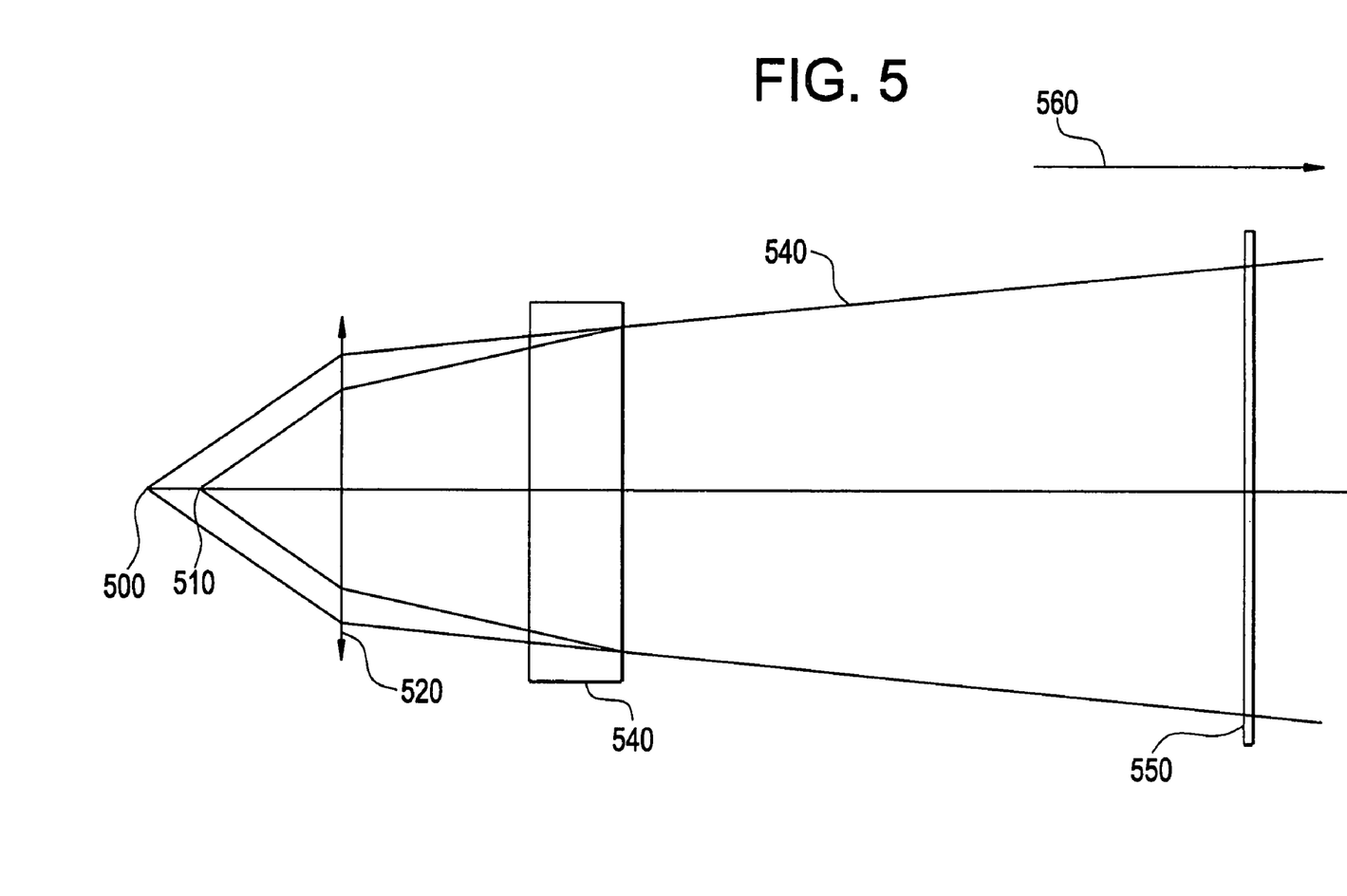
FIG. 5 displays a conceptual drawing of a dual focal plane optics embodiment of the present invention.

FIG. 5 displays a conceptual embodiment of polarization multiplexing implemented in accordance with the teachings of the present invention. Light reflects from two planes. Light from the closer plane 510 passes through objective 520 and through birefringence lens 540, where it is separated into first and second coincident beams of orthogonal linear polarization. The first beam experiences the higher index of refraction of birefringence lens 540 and so will be correctly focused at image plane 560. Said second beam is not correctly focused. Multiplexer 550 selects said first beam and blocks said second beam from the desired portion of said image plane. Light from the farther plane 500 also passes through objective 520 and through birefringence lens 540, where it is separated into a second set of first and second coincident beams of orthogonal linear polarization. Said second beam experiences the lower index of refraction of birefringence lens 540 and so will be correctly focused at image plane 560. Said first beam is not correctly focused. Multiplexer 550 selects said second beam and blocks said first beam from the desired portion of said image plane.

In accordance with the teachings of the present invention, a color beam splitting system is implemented into a measurement and inspection system to create dual focal points. In one embodiment, a color beam splitting method is implemented to make an optical system in which each color corresponds to a different focal plane. In one embodiment, a dichromatic beam splitter is inserted into a beam path. The dichromatic beam splitter separates two colors which then travel along separate paths. Each path has a different focal length negative lens which result in a path length difference that equals the sample substrate thickness. The paths are then recombined to travel to a common image plane. Similar to polarization multiplexing, detection could be performed by dividing a CCD in half with two color filters or using a color filter rotation wheel to alternate the color that is passed to the CCD in time.

Figure 6:
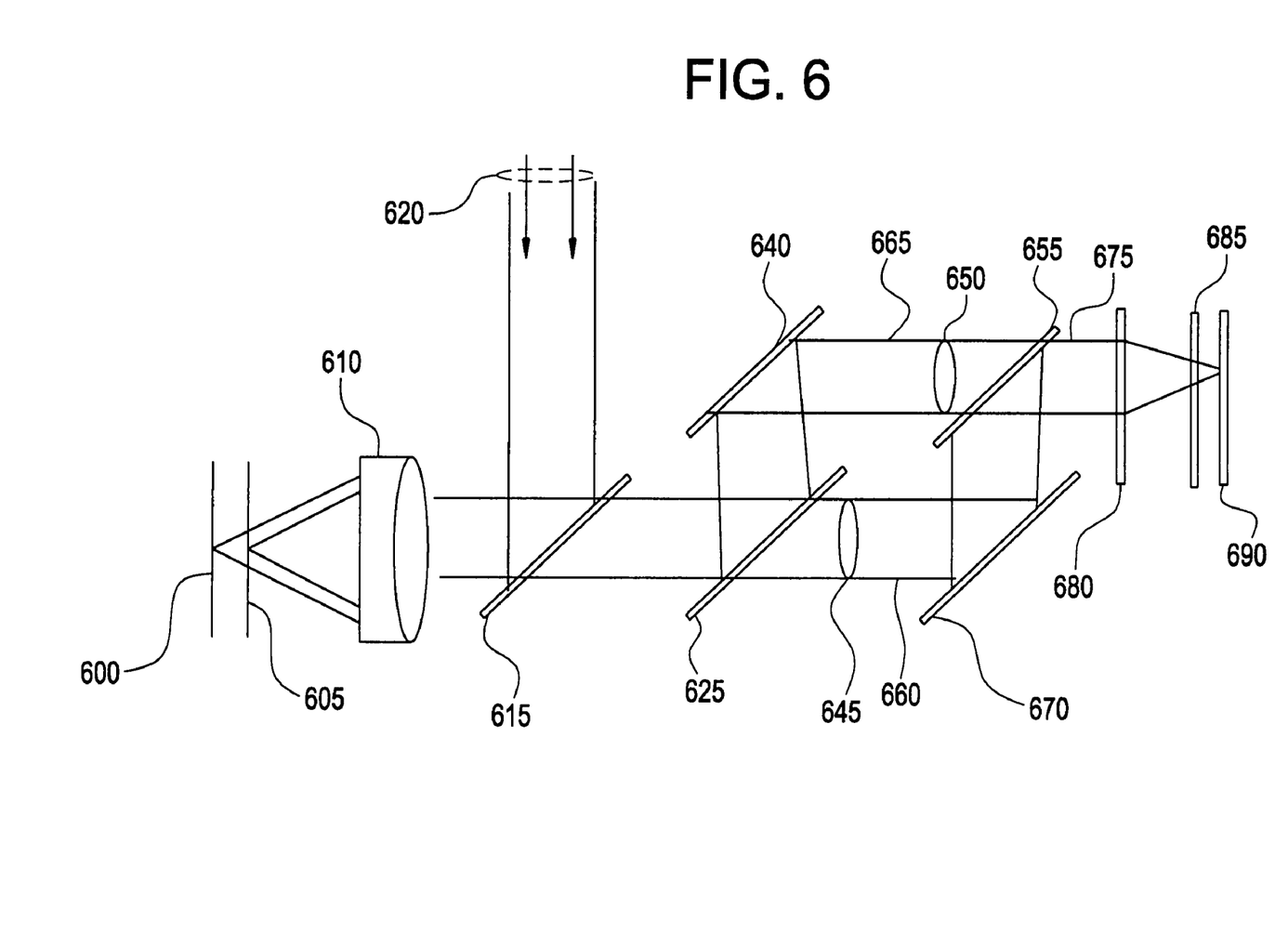
FIG. 6 displays a conceptual drawing of a color filter embodiment of the present invention.

A conceptual color multiplexing diagram is shown in FIG. 6.

Illuminating light 620 enters the system and 50% reflects, the remaining 50% being transmitted to a beam dump and lost, from beamsplitter 615, through objective 610 to illuminate planes 600 and 605 respectively. This light is white or polychromatic, including at least two wavelengths that can be distinguished by dichroic filters. Consider first light reflecting from plane 600. This first light passes to objective 610, where it is focused approximately toward image plane 690. 50% then transmits, the remaining 50% being reflected back toward the illumination source and lost, through beamsplitter 615. This first light then enters the color multiplexer 695 consisting of dichroic filters 625 and 655, mirrors 640 and 670 and first and second lenses 645 and 650, respectively. Said first light, being polychromatic, is separated by dichroic filter 625 into first and second wavelengths or colors, said first wavelength being transmitted and said second wavelength being reflected. Said first wavelength passes through tube lens 645, which adjusts the its focus so that it will focus precisely on image plane 690, reflects from mirror 670 and from dichroic filter 655 and through tube lens 680. Color demultiplexer 685 passes said first wavelength to a certain portion of image plane 690 and blocks it from a certain other portion, so that said first wavelength provides a well focused image of plane 600 on said certain portion of said image plane. Said second wavelength reflects from mirror 640 and passes through tube lens 650, which adjusts the its focus so that it will not focus image plane 690, transmits through dichroic filter 655 and through tube lens 680. Color demultiplexer 685 passes said second wavelength to a second certain portion of image plane 690. Because said second wavelength is not focused on image plane 690, said second wavelength provides background light which, being diffuse and defocused, does not provide any image to said second portion.

In a symmetrical way, light from plane 605 also traverses the optical system, is also separated by the color multiplexer 695 into said first and second wavelengths each of which is transmitted to a separate one of said tube lenses 645 and 650. As a result, said second wavelength provides a well focused image of plane 605 on said second portion of image plane 690, while said first wavelength provides background light which, being diffuse and defocused, does not provide any image to said first portion of image plane 690.

In accordance with the teachings of this invention, the optical paths from the planes 600 and 605 to the image plane 690 must be substantially coincident. This means that the components of the color multiplexer 695 must be so designed that no relative movement or motion that would influence the relative positions of the two wavelengths to a degree greater than that caused by the distortion to be measured can occur. In one embodiment, this may be accomplished by fabricating said color multiplexer on a base of a low expansion metal such as Invar or on a low expansion ceramic material such as Zerodur®. In another embodiment, this may be accomplished by fabricating said color multiplexer by cementing all optical elements into a quasi-monolithic glass assembly.

Figure 7:
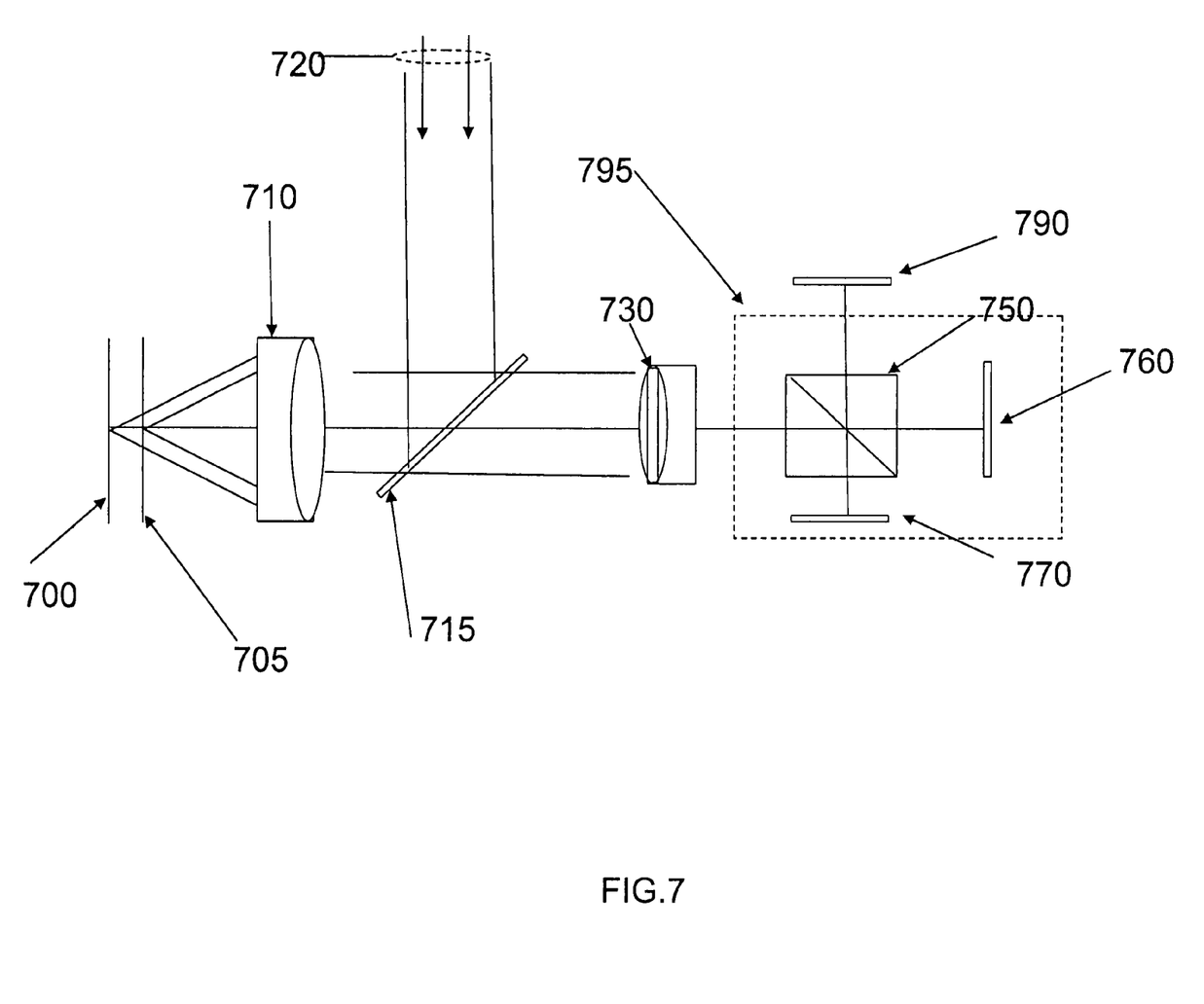
FIG. 7 displays a conceptual drawing of a faux interferometer optics embodiment of the present invention.

FIG. 7. displays a faux interferometer used to implement polarization multiplexing in accordance with the teachings of the present invention. In one embodiment a faux interferometer is implemented where two object surfaces are separated by a given optical path length and are combined into one imaging surface. In order to fold the two surfaces into a common imaging focal plane, a 50/50 beam splitter is introduced into the beam to provide two separate optical paths. The two optical path lengths are offset from each other by a distance that corresponds to the thickness of the sample substrate being measured. These two paths are then recombined to have a common image focal plane as shown below. It should be appreciated that unlike the previous dual focal point imaging schemes mentioned above, this method does not multiplex the two paths therefore in one embodiment, the detector is implemented without demultiplexing.

In FIG. 7 a sample is shown as 700. Illuminating light 720 enters the system and 50% reflects, the remaining 50% being transmitted to a beam dump and lost, from beamsplitter 715, through objective 710 to illuminate planes 700 and 705 respectively. Consider first light reflecting from plane 700. Said first light passes through objective 710, then to beamsplitter 715 where 50% transmits, the remaining 50% being reflected back toward the illumination source and lost, and to tube lens 730 which focuses it towards image plane 790. This first light then enters the faux interferometer 795 consisting of beamsplitter 750 and mirrors 760 and 770. Said first light is separated by beamsplitter 750, 50% being transmitted to mirror 760 and 50% reflected to mirror 770. The distance from beamsplitter 750 to mirror 760 is, for example, shorter than the distance from beamsplitter 750 to mirror 770, so that the portion of said first light that reflects from mirror 760 back to beamsplitter 750, 50% being transmitted back toward the objective and lost, the remaining 50% is reflected to image plane 790 to form a well focused image of Plane 700. The portion of said first light that reflects from mirror 770 back to beamsplitter 750, 50% being transmitted back toward the objective and lost, the remaining 50% is reflected to image plane 790 and provides background light which, being diffuse and defocused, does not provide any image to said image plane.

In a symmetrical way, the second light from plane 705 also traverses the optical system, is also separated by the beamsplitter 750, 50% being transmitted to mirror 760 and 50% reflected to mirror 770. As a result, said second light provides a well focused image of plane 705 on image plane 790, said well focused image consisting of the portion of said second light that reflects from mirror 770 and subsequently reaches said image plane. The portion of said second light that reflects from mirror 760 and subsequently reaches said image plane, being diffuse and defocused, does not provide any image to said image plane.

Note that the images formed by said first and said second light may be arranged to be coincident or adjacent by introducing slight rotation angles, for example less than five degrees, to beamsplitter 750 and mirrors 760 and 770, to one or to more than one, so that the well focused portions of said first and second light fall on the desired locations of image plane 790. Said introduction of angles is performed once during manufacture, said angles being constant and fixed during operation.

In accordance with the teachings of this invention, the optical paths from the planes 700 and 705 to the image plane 790 must be substantially coincident. This means that the components of the faux interferometer 795 must be so designed that no relative movement or motion that would influence the relative positions said first and second light to a degree greater than that caused by the distortion to be measured can occur. In one embodiment, this may be accomplished by fabricating said faux interferometer on a base of a low expansion metal such as Invar or on a low expansion ceramic material. In another embodiment, this may be accomplished by fabricating said color multiplexer by cementing all optical elements into a quasi-monolithic glass assembly.

Finally, the fact that the objects are located at different focus positions requires some image corrections. The first correction is due to the fact that the object to image magnification is different for the two focal planes. To illustrate that problem, let us consider a measurement node with the two objects located respectively at x1 and x2. Their positions on the CCD during the first step of the measurement will be given by $$Y1 = G1 * x1$$

$$Y2 = G2 * x2$$

Where G1 and G2 are the two magnification coefficients for the two focal planes. When repeating the measurement in the second step, both objects may be laterally shifted by a vector dx because, for instance, the vision system was not perfectly centered at the same position on the node. The positions are then now given by:

$$Y1 = G1*(x1+dx)$$

$$Y2 = G2*(x2+dx)$$

So, the fact that both magnifications are different, generates a measurement error whose amplitude is (G1−G2)*dx. It is therefore necessary to calibrate both magnification coefficients and correct the measurements by the differential magnification. Finally, another aspect that may require data corrections is related to the parallax effect. Indeed, both objects being at different focus positions, their apparent distances are affected by an angular misalignment of the vision system. This can be minimized by insuring that angular stability of the vision system remains sufficiently small or by monitoring the angular misalignments of the vision system and make data corrections.

Figure 8:
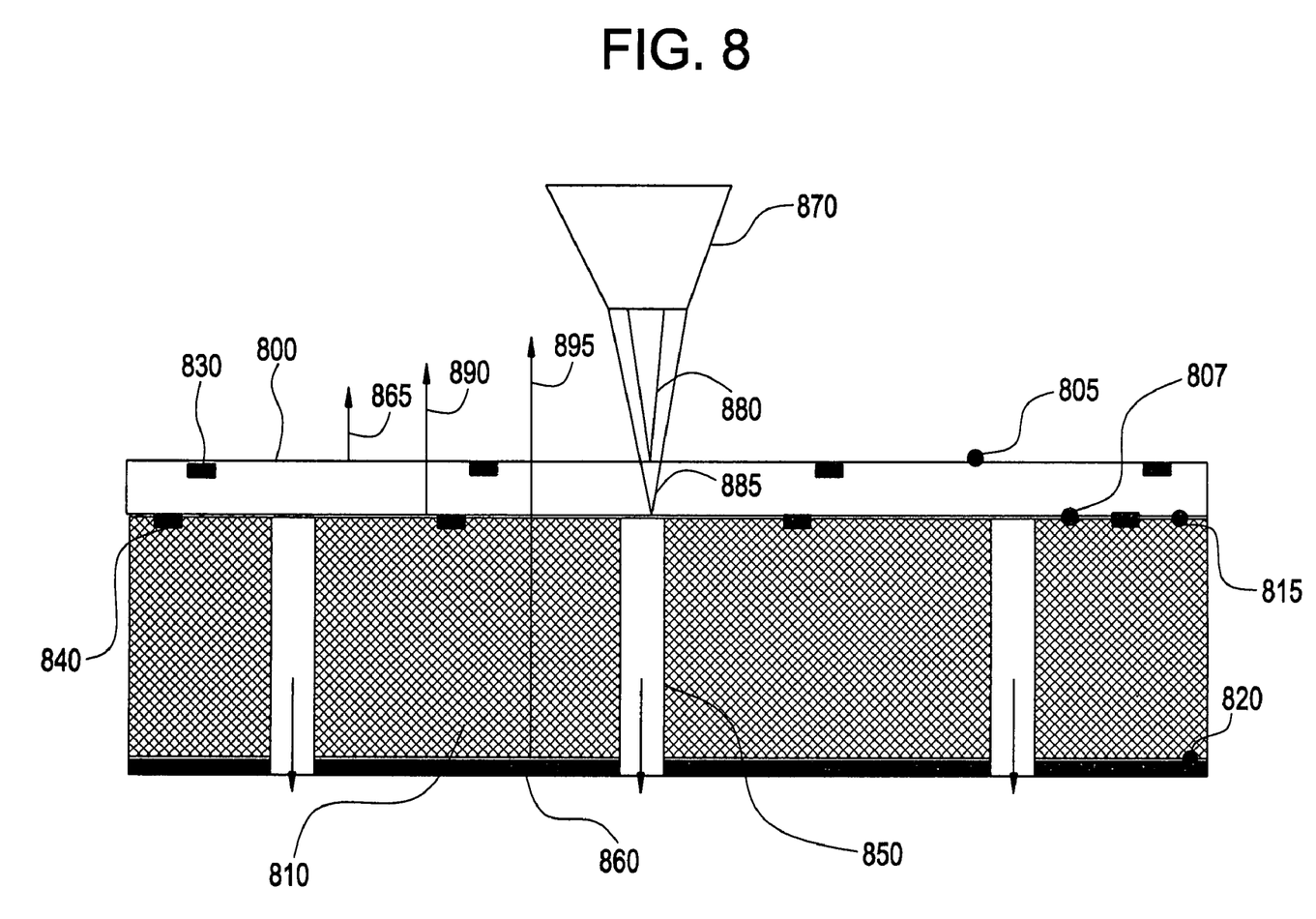
FIG. 8 displays a visual system in combination with a highly reflective surface implemented in accordance with the teachings of the present invention.

FIG. 8 displays a contrast enhancing assembly implemented in accordance with the teachings of the present invention. A sample substrate 800 is shown. The sample substrate 800 includes a topside 805 and an underside 807. The sample substrate 800 is positioned on a reference substrate 810. The reference substrate 810 includes a top side 815 and an underside 820. A highly reflective surface 860 is positioned relative to the underside 820 of the reference substrate 810. The reference substrate 810 includes vacuum ports shown as 850. A first grid pattern 840 is shown on the reference substrate 810. A second grid pattern 830 is applied to the sample substrate 800. A vision system 870 implemented in accordance with the teachings of the present invention. The vision system 870 processes two focal planes (corresponding to light rays 880 and 885) simultaneously. Light rays depicted as 880 are shown to demonstrate processing of a first focal plane at location 805 and light rays depicted as 885 are shown to demonstrate processing at a second focal plane 807.

A quartz halogen white light source used in measurement and inspection systems has a very wide spectral output. Therefore, the spectral transmission of the system is limited by the spectral responsivity of the CCD camera used as the sensor. In one embodiment, the CCD camera has responsiveness from about 350 to 900 nanometers. As a result, the coherency length is given by: $CL = \lambda^2/\Delta\lambda = 0.710$ microns where CL is the coherency length, $\lambda$ is the center wavelength and $\Delta\lambda$ is the spectral width. Therefore, if the gap between the two plates is less than 0.710 microns, interference will occur. This is indeed the case when the sample substrate is being vacuumed to the reference substrate. Therefore, this interference needs to be minimized to provide consistent and accurate measurement results. FIG. 8 displays the reflections generated when using a highly reflective surface 860, such as a mirror. In one embodiment, the highly reflective surface is considered to be an ideal mirror with 100% reflectivity. In one embodiment, the reflection from the topside of the substrate 865 is 4% (i.e., shown as 865). The reflection from the interface of the underside of the substrate 800 and the topside of the reference substrate 810, which is also known as the interference interface, is shown as 890 which is approximately between 0 and 8% (i.e., shown as 890). The reflection from the highly reflective surface is 88% and is shown as 895. The resulting reflection is 96% plus or minus 4%. The worse case variation is 8/92*100=8.7%. In summary the effects of the interference layer can be reduced by a theoretical maximum of 91.3%.

The mirror surfaces reflection overwhelms the effect of the interference between the bottom of the sample LCD substrate 810 and the top of the reference plate 815. The introduction of the highly reflective surface 860 changes the lighting scheme from a bright field reflection to a virtual bright field transmission. This illumination will diminish the effects of surface contamination on the exposed surfaces since their reflective contribution compared to the $4^{th}$ surface is minimal.

Throughout this application, various publications are referenced. The disclosures of these publications in their entireties are hereby incorporated by reference into this application in order to more fully describe the compounds, compositions, and methods described herein.

It should also be understood that while the present invention has been described in detail with respect to certain illustrative and specific aspects thereof, it should not be considered limited to such, as numerous modifications are possible without departing from the broad scope of the present invention as defined in the appended claims.

The invention claimed is:

1. A method of measuring distortion comprising the steps of:
    (a) positioning a first substrate having a first focal plane and a plurality of first markings containing position information in contact with a second substrate having a second focal plane and a plurality of second markings containing position information;
    (b) directing incident light at the first focal plane and the second focal plane so that the incident light reflects from the first focal plane to produce a first beam of light and the second focal plane to produce a second beam of light, the first and second beams of light being coincident and having orthogonal polarization;
    (c) passing the coincident first and second beams of light having orthogonal polarization through a common optical path;
    (d) focusing the coincident first and second beams of light having orthogonal polarization separately on a single image plane;
    (e) simultaneously detecting the first and second beams of light having orthogonal polarization at the single image plane; and
    (f) reproducing the position information contained in the first markings and the second markings from the detected first and second beams of light, respectively, on the single image plane.

2. A method of measuring distortion comprising the steps of:
    (a) positioning a first substrate having a first focal plane and a plurality of first markings containing position information in contact with a second substrate having a second focal plane and a plurality of second markings containing position information;
    (b) directing incident light at the first focal plane and the second focal plane so that the incident light reflects from the first focal plane to produce a first beam of light and the second focal plane to produce a second beam of light, the first and second beams of light being coincident;
    (c) passing the coincident first and second beams of light through a common optical path;
    (d) focusing the coincident first and second beams of light separately on a single image plane;
    (e) simultaneously detecting the first and second beams of light at the single image plane; and (f) reproducing the position information contained in the first markings and the second markings from the detected first and second beams of light, respectively, on the single image plane.

3. A method of measuring distortion as set forth in claim 2, wherein the first beam of light and the second beam of light have orthogonal polarizations.

4. A method of measuring distortion as set forth in claim 3, wherein step (d) comprises the step of placing a low optical power birefringence lens into a nearly collimated region of the coincident first and second beams of light.

5. A method of measuring distortion as set forth in claim 3, wherein step (e) comprises the step of positioning a different polarizer in front of each half of a detector, whereby one side of the detector receives light with one direction of polarization and the other side of the detector receives light with another direction of polarization.

6. A method of measuring distortion as set forth in claim 3, wherein step (e) further comprises the step of positioning a switching device between the first and second focal planes and the single image plane and positioning a detector at the single image plane, whereby the detector alternatively detects one polarization direction and then the other polarization direction as a function of time.

7. A method of measuring distortion as set forth in claim 2, wherein the first beam of light and the second beam of light are of different colors.

8. A method of measuring distortion as set forth in claim 2, wherein step (d) further comprises separating the first and second beams of light, directing each of the first and second beams of light along a different predetermined optical path length, and recombining the first and second beams of light at a single image plane.

9. A method of measuring distortion as set forth in claim 2, further comprising correcting the position information contained in the first markings and the second markings from the detected first and second beams of light, respectively, to take into account a differential magnification factor between the first and second focal planes.

10. A method of measuring distortion as set forth in claim 2, wherein step (b) through (f) are implemented using a dual focal plane vision system, and further comprising either minimizing an angular misalignment of the dual focal plane vision system to avoid parallax effect or monitoring the angular misalignment of the dual focal plane vision system and correcting the position reproduced in step (f) for parallax effect.

11. A method of measuring distortion as set forth in claim 2, wherein step (b) through (f) are implemented using a dual focal plane vision system comprising an illumination optics system having an illumination numerical aperture and an imaging optics system having an image numerical aperture, and wherein the illumination numerical aperture is greater than the image numerical aperture.

12. The method of measuring distortion as set forth in claim 2, further comprising:
(g) positioning a reflective surface a farther distance from the single image plane than the first focal plane and the second focal plane are to the single image plane; and
(h) reflecting the incident light of step (b) off of the reflective surface back to the single image plane.

13. A method of measuring distortion as set forth in claim 12, wherein the first beam of light and the second beam of light have orthogonal polarizations.

14. A method of measuring distortion as set forth in claim 13, wherein step (d) comprises the step of placing a birefringence lens into a nearly collimated region of the coincident first and second beams of light.

15. A method of measuring distortion as set forth in claim 13, wherein step (e) comprises the step of positioning a different polarizer in front of each half of a detector, whereby one side of the detector receives light with one direction of polarization and the other side of the detector receives light with another direction of polarization.

16. A method of measuring distortion as set forth in claim 13, wherein step (e) comprises the step of positioning a switching device between the first and second focal planes and the single image plane and positioning a detector at the single image plane, whereby the detector alternatively sees one polarization direction and then the other polarization direction as a function of time.

17. A method of measuring distortion as set forth in claim 12, wherein the first beam of light and the second beam of light are of different colors.

18. A method of measuring distortion as set forth in claim 12, wherein step (d) comprises separating the first and second beams of light, directing each of the first and second beams of light along a predetermined optical path length, and recombining the first and second beams of light at the single image plane.

* * * * *